(12) United States Patent
Riffe (10) Patent No.: US 6,681,614 B1
(45) Date of Patent: Jan. 27, 2004

(54) APPARATUS FOR TESTING CO-EFFICIENT OF FRICTION OF A ROAD SURFACE

(76) Inventor: Daniel L. Riffe, 3088 Lake Hollywood Dr., Los Angeles, CA (US) 90068

( * ) Notice: Subject to any disclaimer, the term of this patent is extended or adjusted under 35 U.S.C. 154(b) by 4 days.

(21) Appl. No.: 09/948,849

(22) Filed: Sep. 6, 2001

Related U.S. Application Data (60) Provisional application No. 60/230,360, filed on Sep. 6, 2000.

(51) Int. Cl.[7] ............................................. G01N 19/02
(52) U.S. Cl. .................................................. 73/9; 73/8
(58) Field of Search .................................. 73/9; 701/80

(56) References Cited

U.S. PATENT DOCUMENTS

| | | | | |
|---|---|---|---|---|
| 3,301,039 A | * | 1/1967 | Kummer | 73/9 |
| 3,538,742 A | * | 11/1970 | Benning | 73/9 |
| 3,884,502 A | * | 5/1975 | Wagner | 280/423 R |
| 4,130,008 A | * | 12/1978 | Broshears | 73/9 |
| 4,202,454 A | * | 5/1980 | Browne et al. | 213/86 |
| 4,315,426 A | * | 2/1982 | Brandon | 73/9 |
| 4,662,211 A | * | 5/1987 | Strong | 73/9 |
| 4,779,447 A | * | 10/1988 | Rath | 73/9 |
| 4,909,073 A | * | 3/1990 | Takahashi et al. | 73/146 |
| 4,958,512 A | * | 9/1990 | Johnsen | 73/9 |

* cited by examiner

Primary Examiner—Hezron Williams
Assistant Examiner—Charles Garber
(74) Attorney, Agent, or Firm—Frank L. Zugelter (57) ABSTRACT

An apparatus (20) for testing the co-efficient-of friction of a road surface (78) of a road (79) including a electronic digital device (22) that senses through its sensor (75) the speed of a toothed sprocket wheel (71) and by which through the dropping of a frame (24) by means of a tripping mechanism (80) that trips upon a rotating motor (34) accelerating and by which a predetermined value in device (22) is reached by the speed of a tire flat (61) that strikes road surface (78).

8 Claims, 8 Drawing Sheets

APPARATUS FOR TESTING CO-EFFICIENT OF FRICTION OF A ROAD SURFACE

This invention relates to U.S. Provisional application Ser. No. 60/230,360, filed Sept. 6, 2000.

TECHNICAL FIELD

This invention relates to testing apparata and in particular to an apparatus that provides for an accurate and precise indication of the co-efficient of friction on a road's surface from a gauge-reading in the apparatus which indicates the coefficient of friction of a road's surface to rubber on a rubber tire of a moving vehicle on the road.

BACKGROUND TO THE INVENTION

The highway department of the State of California, CalTrans, has used an apparatus of this kind since the 1960's, and this apparatus is an improvement over the CalTrans apparatus. This apparatus is unique in the sense that no other device of this nature is known except the old one of CalTrans and this improvement over it.

The needs the invention addresses and satisfies in this kind of apparatus are increased dependability, accuracy, and ease of operation.

SUMMARY OF THE INVENTION

The invention is in an apparatus, stationary in operation, that provides accurate measurement of speed and control by a digital speed control in electronic control circuitry on a rotating tire through its sensor, to sense the tire speed. An accurate, precise reading of the coefficient-of-friction of a road's surface is achieved. A mechanism trips a cocked bell-crank assembly that includes a bearing that is freed from its cocked position by an energized solenoid the action of which simultaneously drops the rotating tire upon the road surface being tested. A digital electronic control circuit manually initiated conducts the test automatically.

An object of this invention is to provide a dynamic testing reading from an apparatus in a static environment, such as standing in a stationary manner, without the need for the testing apparatus to be moving along a roadway.

Another object of the invention is to provide for an automated operation of an apparatus that tests for co-efficient of friction of a road surface.

A further object of this invention is to provide substantial savings in the cost of conducting a co-efficient-of-friction test by the apparatus of this invention.

A still further object of this invention is to provide portability for positioning at various stationary locations the apparatus and by which it is ready with ease for immediate operation in a next stationary location.

These and other objects and advantages of the invention will become more apparent upon a full and complete reading of the following description, the appended claims thereto and the accompanying drawing comprising seven (7) sheets of ten (10) FIGURES.

BEST MODE FOR CARRYING OUT THE INVENTION

Figure 1:
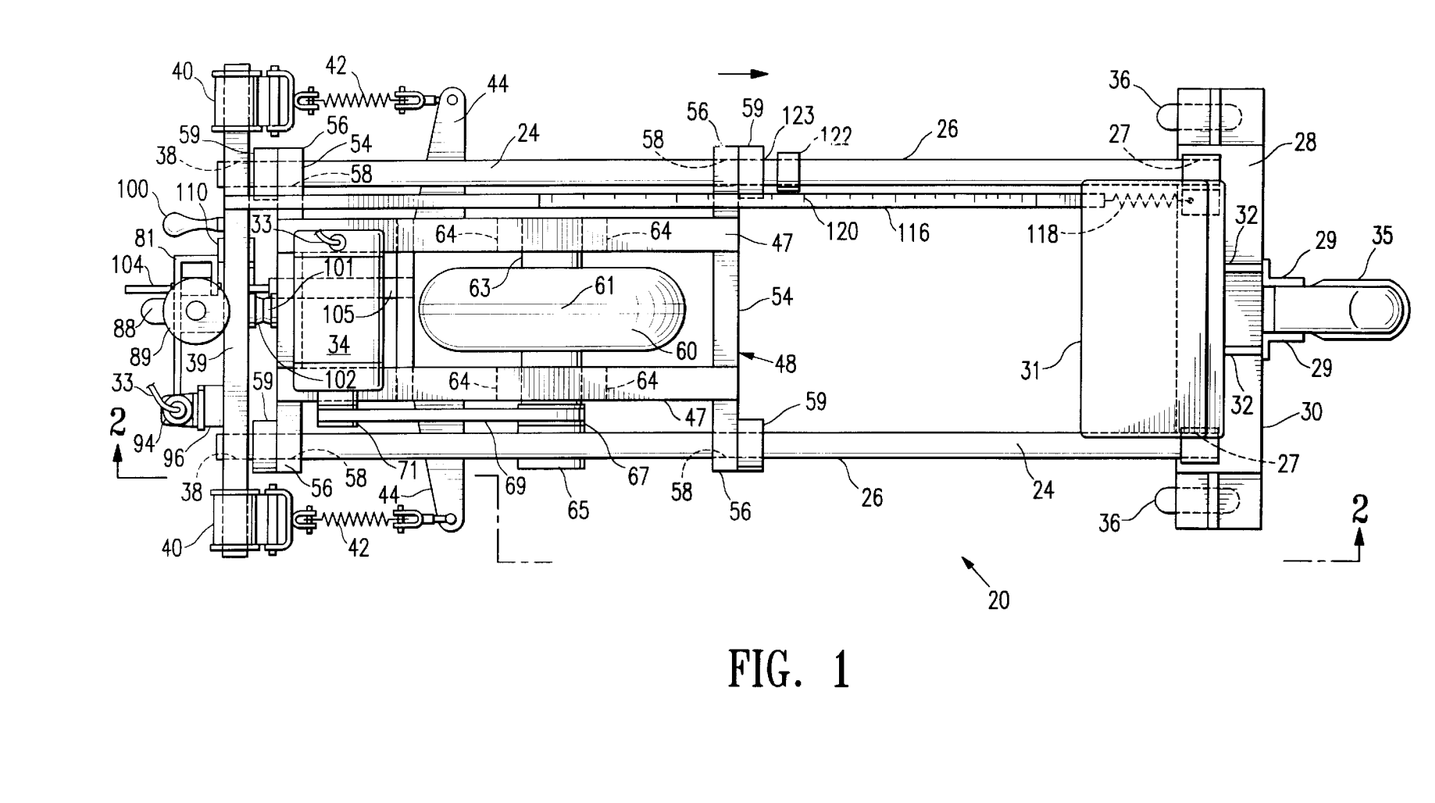
FIG. 1 is a plan view of the apparatus of this invention, in its cocked or O-position.
Figure 2:
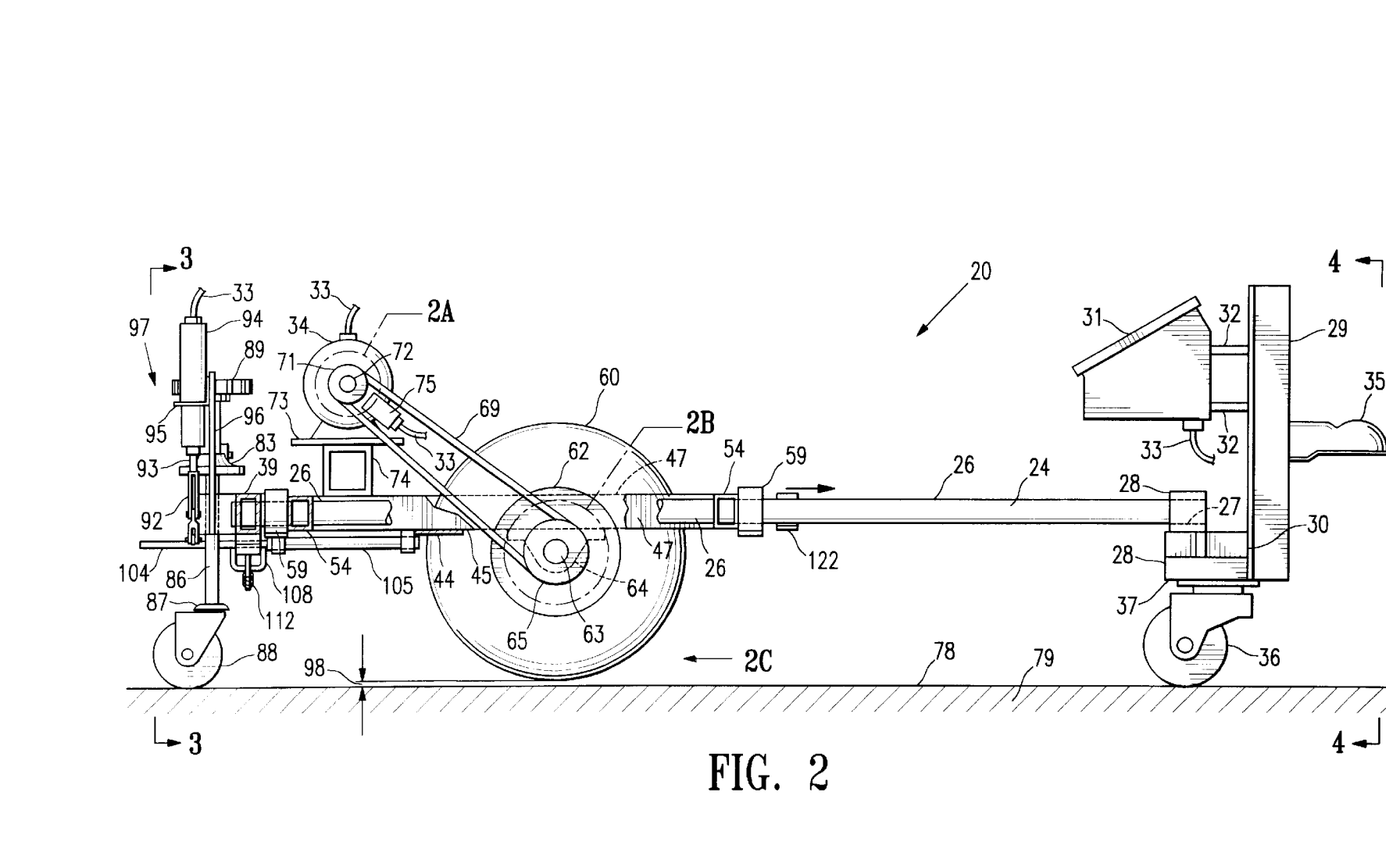
FIG. 2 is an elevational view of the apparatus taken on line 2—2 of FIG. 1, the apparatus in its cocked or O-position.
Figure 4:
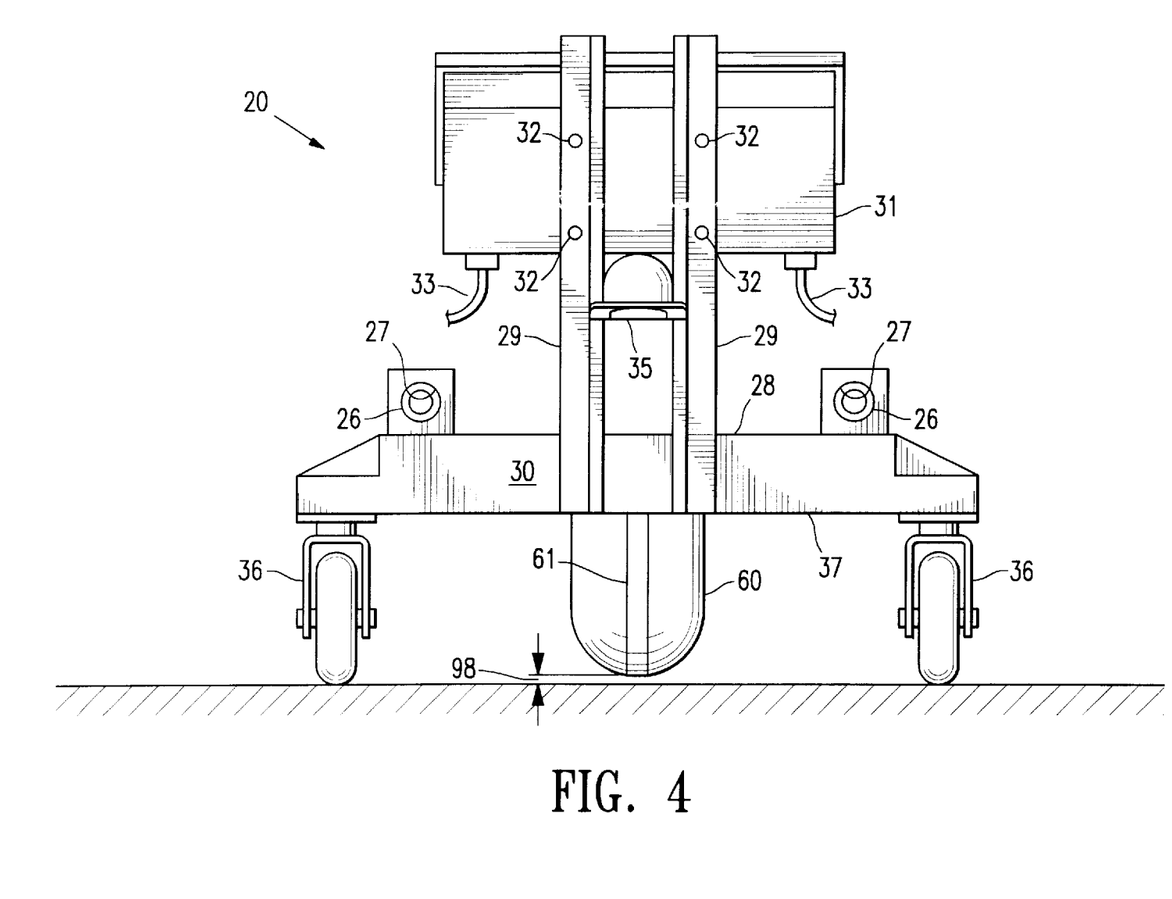
FIG. 4 is a front elevational view of the apparatus of FIGS. 1, 2, and 3.
Figure 5:
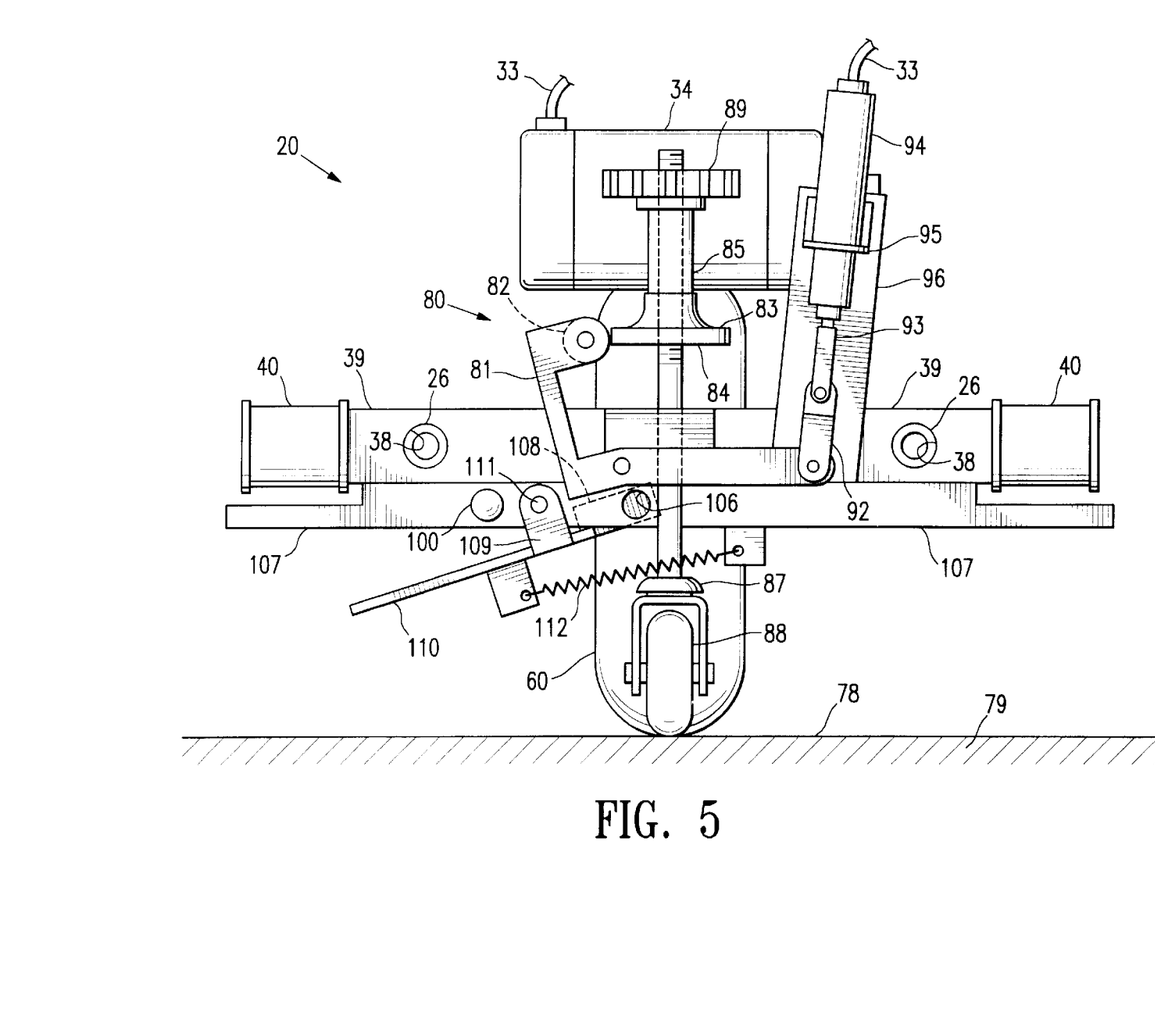
FIG. 5 is a rear elevational view of the apparatus in a mode in which its rotating tire is in contact with a road surface.
Figure 6:
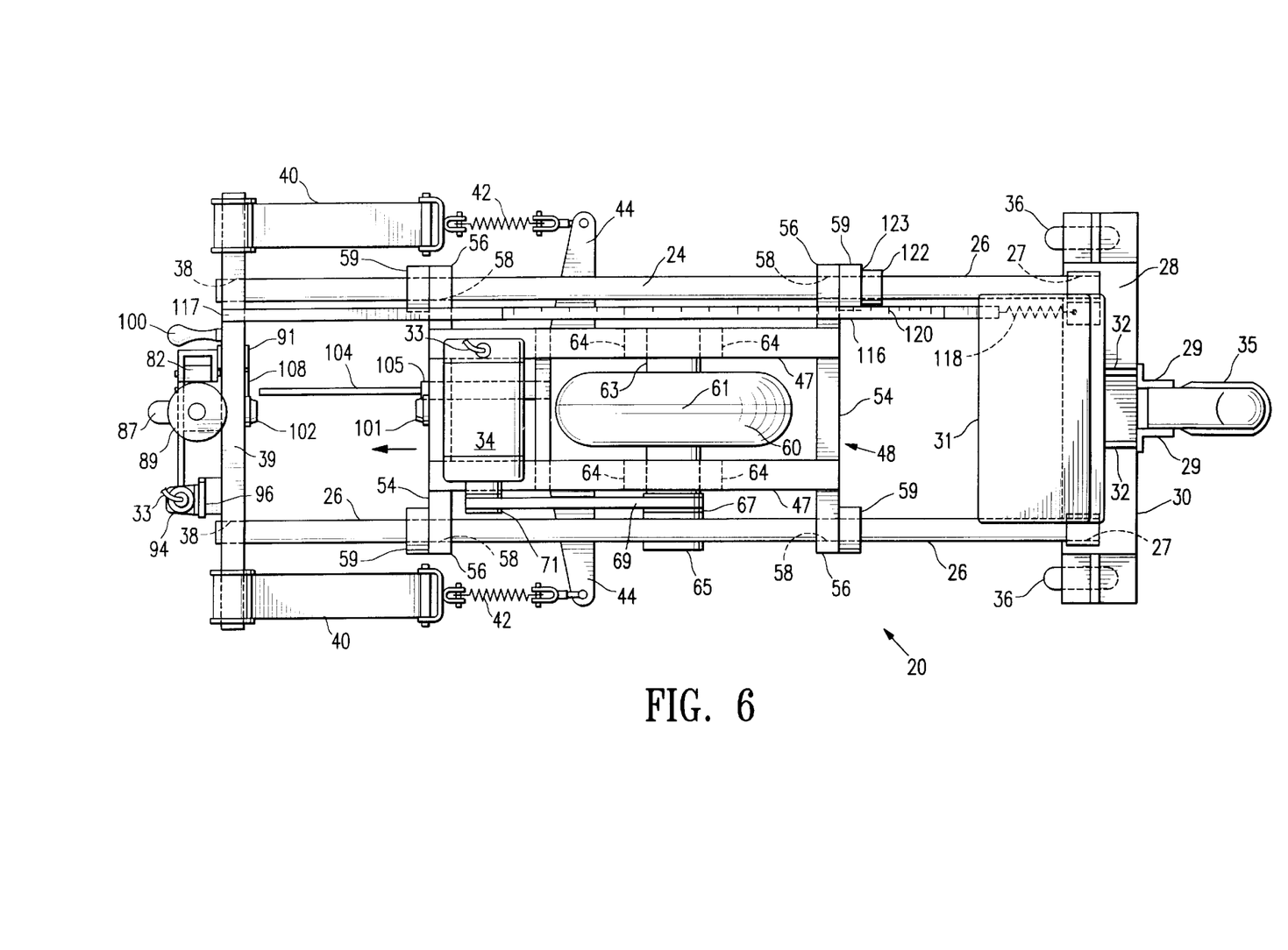
FIG. 6 is a plan view of the apparatus of the invention in a mode at or after the tire has engaged a road surface.
Figure 7:
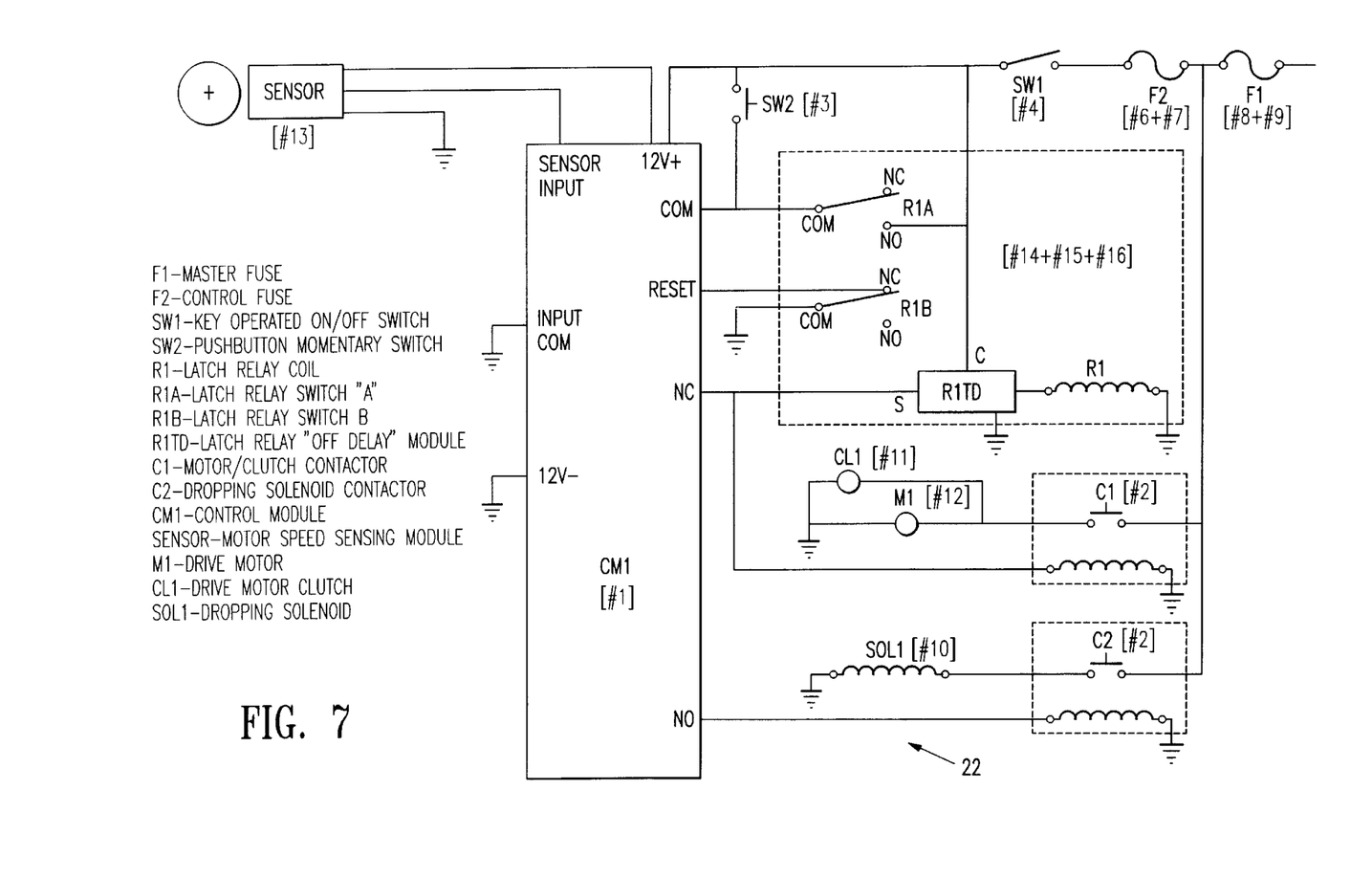
FIG. 7 is a schematic drawing of an electronic control circuit for operation of the automatic apparatus.

Referring now to the drawing wherein reference characters correspond to like numerals hereinafter in the following description, FIGS. 1–6 illustrate an apparatus 20 embodying the invention. FIG. 7 illustrates an electronic circuit 22, FIG. 7, for operating apparatus 20. Apparatus 20 includes a frame 24, FIGS. 1, 2, 6, formed by a pair of spaced tubular members 26 each of which, at the front end of apparatus 20, is fixed in relationship to each other by their ends being securely mounted in their corresponding bores 27 which are in stepped-up parts of a solid one-piece metal casting 28. A pair of spaced upright angled-iron members 29 are fixed to a front wall 30, FIGS. 1, 6, of casting 28. An electronic control console 31 is fixedly supported by a pair of rigid arms 32, FIGS. 1, 2, securely mounted to the rearward sides of upright members 29 and in which elements of circuit 22 are disposed, with the collection 33 of the circuit's wirings, FIGS. 2, 3, 4, 5, 6, emanating from various points of the console's housing to, for example, a motor 34, FIGS. 1, 2, and to their other corresponding elements in FIGS. 1, 2, 3, 5, 6, by which apparatus 20 is energized for operation. A hitch assembly 35, FIGS. 1, 2, 6, is securely mounted to the forwardly extending sides of and between upright members 29 and by which apparatus 20 is held stationary during a testing operation. Front swivel caster assemblies or standards 36 are suitably located exteriorly, FIGS. 1, 2, 4, of tubular members 26, each being securely fixed to the underside 37, FIG. 2, of solid casting 28 and by which ease of portability from one stationary point to another for apparatus 20 is provided.

Figure 3:
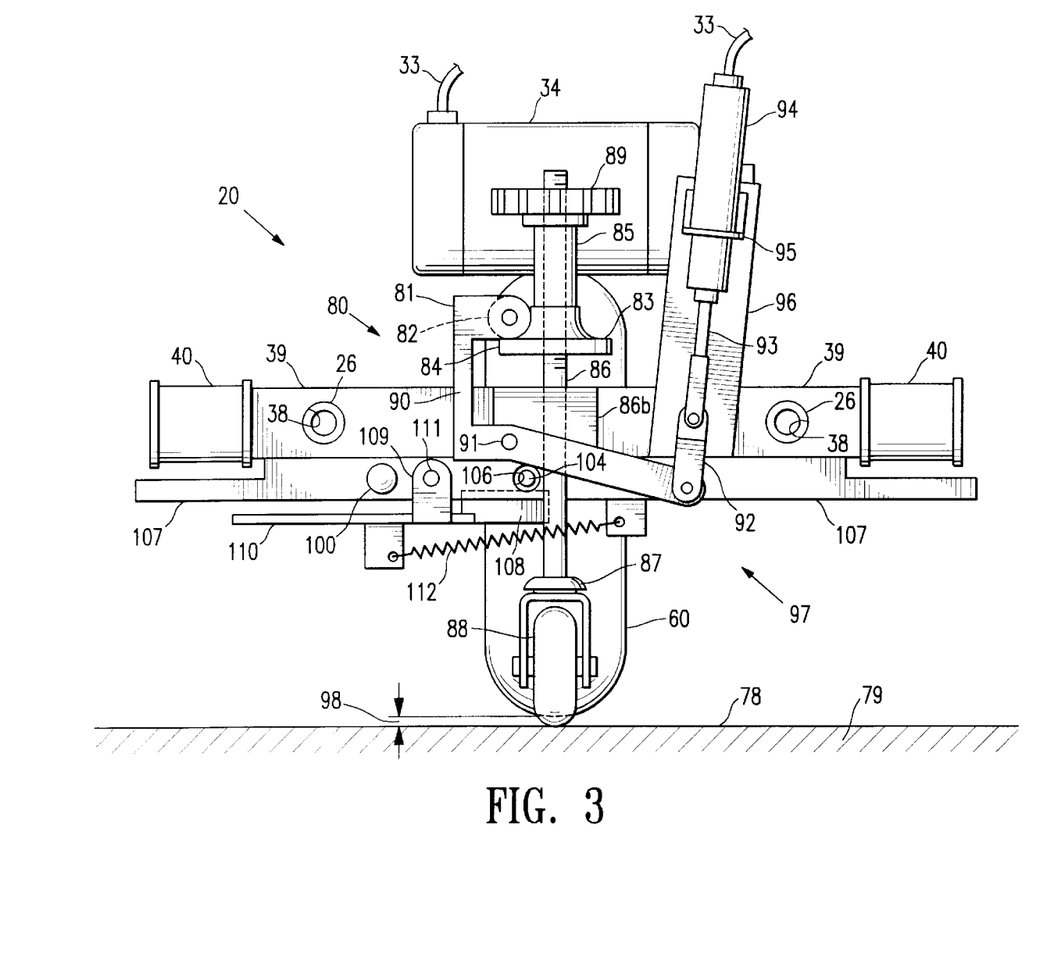
FIG. 3 is a rear elevational view of the apparatus taken on line 3—3 of FIG. 2, in a mode in which its rotating tire is not in contact with a road surface.

At the rear end of apparatus 20, FIGS. 1, 2, 3, each of tubular members 26 is suitably securely mounted in bores 38 formed in a rigid metal casting 39 and by which tubular members 26 remain in planar and parallel orientation in their spaced relationship. Metal casting 39 projects laterally beyond each tubular member 26 for a fixed mounting adjacent each of its ends of constant-force coiled spring assemblies 40. Open ends of the springs in assemblies 40 are correspondingly suitably connected or hooked by spring assemblies 42, FIG. 1, to their respective transversely extending brackets 44, FIGS. 1, 2, securely fixed to an underside 45, FIG. 2, of their corresponding spaced rectangular tubings 47 of and extending longitudinally within a carriage 48, FIG. 1, at equally distanced points along its length, FIGS. 1, 6.

In carriage 48 the opposite ends of tubings 47 are securely mounted in bores (not called out) formed in front and rear cross-struts 54, FIG. 1, 6, of carriage 48. Cross-struts 54 include integral extensions 56 extending laterally beyond tubings 47 and in which bores 58 are formed. Bearing carriers 59 for carriage 48 are slidably mounted on tubular members 26 and are securely attached to the four (4) cross-struts 54 for sliding and reciprocating carriage 48 along frame 24 in the operation of apparatus 20.

Figure 2A:
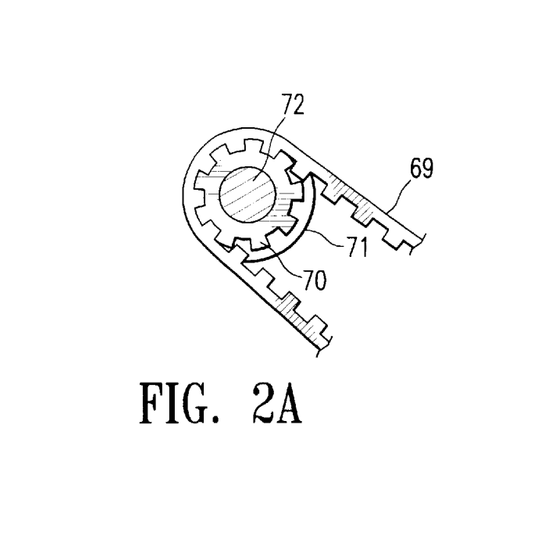
FIG. 2A is an enlarged fragmentary diagrammatic view taken at the end of line 2A in FIG. 2, illustrating a toothed sprocket wheel on the shaft of a motor in the apparatus and its pulley belt.
Figure 2B:
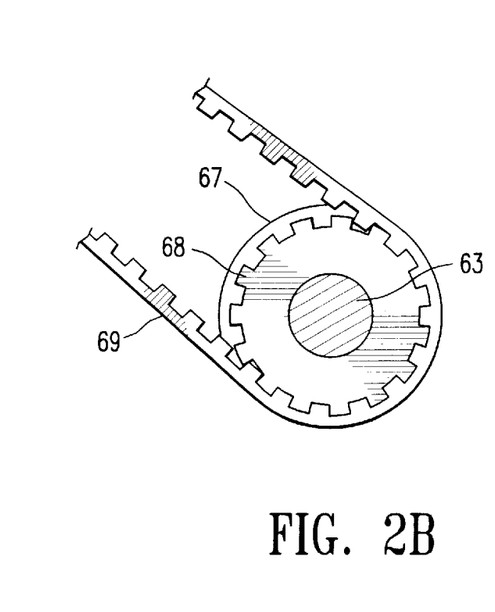
FIG. 2B is an enlarged fragmentary diagrammatic view taken at the end of line 2B in FIG. 2, illustrating a tire axle's sprocket wheel to which the pulley belt illustrated in FIG. 2A is applied.
Figure 2C:
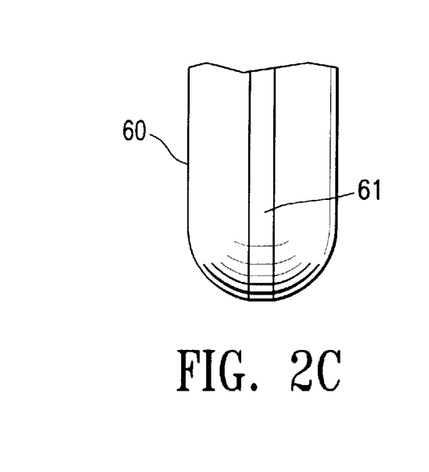
FIG. 2C is an enlarged end view taken in the direction of arrow 2C in FIG. 2 of a tire on which a flat portion is illustrated on the tire's periphery or greatest radius from the axis of a wheel on which the tire is securely mounted.

Generally midway of the length of and in the space between tubings 47 and spaced cross-struts 54, an air-filled rubber tire 60, having a sufficiently wide flat width or flat 61, FIG. 2C, for testing purposes in its periphery or greatest radius, is disposed. Tire 60 is conventionally mounted to its wheel 62, FIG. 2, that is rotatable with its axle 63 maintained outside the plane of tubings 47 and cross-struts 54 by it being rotatably mounted in depending brackets 64 securely mounted on each of tubings 47, FIG. 2. FIG. 2 illustrates the axis of axle 63 being below the plane of tubings 47 and cross-struts 54. An electrical clutch 65, FIGS. 2, 6, is securely mounted adjacent the one end of axle 63, FIGS. 2, 6, along with a sprocket wheel 67, FIG. 2B, suitably securely mounted on axle 63 to the interior side, FIG. 1, of electrical clutch 65. Sprocket wheel 67 includes teeth 68, FIG. 2B, which cooperates with a toothed pulley belt 69 that extends to and which cooperates with teeth 70 on a sprocket wheel 71 suitably secured to a shaft 72, FIG. 2A, of motor 34 and by which combination a synchronous relationship is established. Motor 34 is securely mounted on a support base 73 securely mounted on a spacer member 74 which in turn is suitably securely mounted to the tubings 47 of carriage 48. It should be understood that in the testing operation of apparatus 20 that the collection of wirings 33 which extends between console 31 and elsewhere along apparatus 20, for example, to motor 34, is of flexible insulated nature and are harnessed together or otherwise safely secured along the length of apparatus 20 out of the way of movement of carriage 48 and motor 34 to prevent interference of such wirings with any element of apparatus 20 that is in motion in its testing operation.

Immediately next to teeth 70 of sprocket wheel 71, FIG. 2, a timing sensor 75 is employed to count the number of teeth 70 that passes it in a given period of time. Sensor 75 is suitably fixed on the end of the housing of motor 34 in its location in proximity to teeth 70. The motion of teeth 70 passing in proximity to sensor 75 generates a signal in the sensor which is transmitted by the wiring 33 to Central Module CM1, #17 in FIG. 7, which processes that signal and compares the rotational speed corresponding to that signal to the programmed value within CM1 and corresponding to the rotational speed of tire 60 required by the apparatus 20, to obtain accurate and precise results indicating the correct co-efficient of a road surface 78 of road 79, FIG. 2. FIGS. 2A, 2B diagrammatically illustrate the teeth 68, 70 in the operation of apparatus 20, In the preferred embodiment, twenty-two (22) teeth are the actual number of teeth 70 on sprocket 71 about the motor's shaft 72 and thirty (30) teeth are the actual number of teeth 68 on sprocket 67.

At the rear of and in the operation of apparatus 20, a mechanism 80, FIGS. 1, 2, 3, is provided to trip or release tire 60 from its elevated position above road surface 78 as it is rotating at its appropriate and measured speed in the testing operation upon road 79. Mechanism 80, FIG. 3, includes a bell-crank assembly 81 to one end of which is attached a roller bearing 82 which seats upon a ledge or latch 83 in a cocked position for mechanism 80. Ledge or latch 83 is formed on an outwardly extending element 84 of a sleeve 85 threaded to a threaded stem 86 supported in a block 86b formed in casting 39 at the bottom of which a swivel caster assembly or standard 87 is securely mounted to its caster wheel 88 adapted for engaging the road surface 78 in the testing operation. Assembly 81 includes an arm 90, FIGS. 3, 5, connected to roller bearing 82 and which is pivotally mounted, as at 91, FIG. 3, to metal casting 39 of frame 24, below ledge 83, arm 90 extending in its length to the other side of pivot point 91 to join linkage 92 that is attached to the shaft of a pull rod or shaft 93 of a solenoid 94 its housing being captured in an opening of an L-shaped bracket 95 securely mounted to a support bar 96 that in turn is securely mounted to metal casting 39 of frame 24. Pull rod or shaft 93 retracts in the apparatus' operation to uncock or release roller bearing 82 from ledge or latch 83, with the pivoting action at pivotal mount 91 on arm 90 occurring, and thereby providing for the simultaneous dropping of the entire rear end 97 of apparatus 20 pivotal at the axles of caster assemblies or standards 36, FIG. 2, and by which tire 60 drops on to road surface 78.

A span 98 of distance, FIGS. 2, 3, 4, between tire flat 61 and road surface 78 must exist in the cocked position and condition for mechanism 80, for apparatus 20 to properly operate. With tripping mechanism 80 first placed in its cocked position and condition, and (rear) caster assembly 87 engaging a point or patch on road surface 78 at which testing is to take place, handle 89 on threaded stem 86 is turned to lower or raise mechanism 80 towards or away from road surface 78, thereby changing span 98 until it is properly set. The action of turning handle 89 to properly set span 98 carries with it the lowering and raising of frame 24 by reason of its connection to mechanism 80 through (rear) metal casting 39, support bar 96 secured to metal casting 39, solenoid 94 on support bar 96, and bell-crank assembly 81 connected to solenoid 94 as described above.

It should be noted in FIG. 3, that although caster wheel 88 is engaging road surface 78 tire 60 is not, while in FIG. 5, tire 60 is engaging road surface 78 as a result of the uncocking of mechanism 80 through the release of end or roller bearing 82 from ledge or latch 83 which occurs in the operation of apparatus 20, more fully described hereinafter. To place apparatus 20 in its cocked position or condition, i.e., raising roller bearing or end 82 so it grips ledge or latch 83, a lifting knob 100, FIGS. 6, 5, secured to (rear) metal casting 39 for cocking mechanism 80, is grasped to raise frame 24 so that the bell-crank assembly's end or roller bearing 82 seeks and seats on ledge or latch 83 as lifting knob 100 raises frame 24.

In a cocked mode for apparatus 20, i.e., apparatus 20 is in an O-position, FIG. 1, carriage 48 is at its rearward location, FIG. 1, in frame 24, with rear bearing carriers 59 adjacent to metal casting 39, while a resilient or rubber stop 101, FIGS. 1, 6, is securely mounted centrally of rear cross-strut 54. A like resilient or rubber stop 102 is securely mounted centrally of metal casting 39 of frame 24 and abuts stop 101. Further, a hydraulically-actuated piston rod 104, FIGS. 1, 2, 6, of a hydraulic cylinder 105, projects through a hole 106 formed in a rectangular metal member 107, FIG. 3, that is bolted to metal casting 39. A door 108 is provided for hole 106, it being an extension of one of two ears 109 having its door-operating lever 110, FIG. 3, pivotally mounted at 111 to metal member 107. As illustrated in FIG. 3, door lever 110 is in its upper position against the action of a spring 112 which otherwise biases door 108 across hole 106. By manually holding lever 110 in its upper position, wherein its action acts against the bias of spring 112, door 108 is pulled from across hole 106, hole 106 is opened, and piston rod 104 projects through hole 106, and the resilient stops 101, 102 seat against each other. When carriage 48 shoots forward on frame 24 in the operation of apparatus 20, piston rod 104 and its hydraulic cylinder 105 go with it. As soon as piston rod 104 passes back through hole 106, the biasing action of spring 112 closes door 108 over it. In the reaction occurring upon completion of a test in the operation of apparatus 20, in which carriage 48 reacts rearwardly under the influence of the extended or uncoiled constant-force coiled spring members 40 re-coiling, hydraulic cylinder 105 absorbs the force of the piston rod 104 striking closed door 108. Consequently, with piston rod 104 abutting door 108, carriage 48 comes to a halt or stop about six (6) inches from its O-position relative to frame 24 due to the absorption by cylinder 105 of the force of impact of rod 104 on door 108. Then by manually raising lever 110, door 108 rotates out of abutment with hole 106 and thereafter, piston rod 104 is able to project through hole 106, with carriage 48 sliding along tubular members 26 until stops 101, 102 seat at or abut one another. Thereafter by manually raising lifting knob 100, end 82 of bell-crank assembly 81 can reach its ledge 83 to again place apparatus 20 in its O-position illustrated in FIGS. 1 and 3.

The O-position of apparatus 20 prepares it for measuring the coefficient of friction of the road surface 78 upon release of cocking mechanism 80 and the dropping of rotating tire 60 on to road 79 as a result of such release. A straight, flat gauged tape 116, FIG. 1, extends from its one secured end 117, FIG. 6, at rear metal casting 39 of frame 24 towards metal casting 28 to which it is connected by a spring 118 that maintains tape 116 in a straight and flat manner for the purpose of obtaining a reading on one of the measured graduations 120, along tape 116 in the operation of apparatus 20. Both planes, vertical and horizontal of tape 116, are parallel to the corresponding vertical and horizontal planes for tubular members 26 and tubings 47 of carriage 48 so that an accurate reading on tape 116 occurs in a testing operation.

Tape 116 cooperates with an indicator 122, FIG. 1, in the form of a collar, slidably mounted on the one tubular member 26 adjacent to it. Indicator 122 works with carriage 48 in a testing operation. It is initially set against a reference point 123 at the beginning of a test, the reference point being provided by its associated bearing carrier 59, FIG. 1, while being slidably mounted along the one tubular member 26. As carriage 48 shoots forward on tubular members 26 in a testing operation, reference point 123 also correspondingly shoots forward, carrying forward as well indicator 122 abutting against it in such movement. At the extreme point of thrust for carriage 48 in its forward movement, indicator 122 remains at such extreme extent pointing to a correlative reading on the adjacent tape 116 while the constant-force coiled springs 40 retract carriage 48 and all the bearing carriers 59.

Circuit Description and Operation

Activation of electronic circuitry 22, FIG. 7, elements of the circuitry being suitably supported in console 31, and from which console 31 separate wirings 33 extend to the electrical components in apparatus 20 which functions through their particular wiring 33, controls the process of operation of apparatus 20 in a testing for the co-efficient of friction on a road surface 78 of road 79. Description and explanation of operation of the circuitry, FIG. 7, follows.

The following describes only the Positive (+) side of the circuitry. Negative (−) leads are omitted for simplicity. And negative leads not shown return to ground and/or the negative terminal of the power source.

Electric power (12V DC+) enters the circuit Master Fuse (F-1) [#8+9] and continues to the following:
 1. Normally Open (NO) terminal of Contactor C1 [#2].
 2. Normally Open (NO) terminal of Contactor C2 [#2].
 3. Control Circuit Fuse (F2) [#6+7].

Control Fuse F2 is connected to a key-operated On/Off switch SW1 [#4]. The closing of SW1 arms the circuit and provides power to the following:
 1. Push-button Momentary Switch SW2 [#3].
 2. Power Input Terminal (12V+) of the Control Module CM1 [#1].
 3. Normally Open (NO) Terminal of Switch A of Latch Relay 1 (R1A) [#14+15+16].
 4. Coil Terminal C of Off Delay Timer R1TD [#14+15+16] of Latch Relay R1.

Momentary closing of SW2 begins a cycle by providing power to the following:
 1. Common Terminal (Com) of the output section of CM1.
 2. Common Terminal (Com) of Switch A of Latch Relay 1 (R1A). Through the Com Terminal of CM1, power is provided, within CM1 to its Normally Closed (NC) Terminal and from it, to:
 1. Shunt Terminal (S) of R1TD.
 2. Coil windings of Motor/Clutch Contactor C1.

Upon receiving power at S, R1TD conducts power from C to the R1 coil [#14], causing both of the R1A and R1B [#14+15+16] switches to transfer from Normal position to the Not-Normal position, resulting in the following two events:
 1. The transfer of R1A provides a pathway for power to COM of CM1, bypassing SW2. This establishes a latch, keeping the R1 coil energized and both R1A and R1B switches in the Not-Normal position.
 2. The transfer of R1B breaks a connection to ground at the CM1 Reset terminal.

Upon receiving power, the coil of C1 energizes and the C1 NO contacts are closed, providing power to the drive motor (M1) [#12] and electric clutch (CL1) [#11], beginning the acceleration of the drive wheel. As M1 accelerates, the SENSOR [#13] senses the movement of the motor pulley and provides a digital signal that is proportional to the speed of M1 to the Sensor input of CM1. CM1 analyzes this signal and compares it to a programmed value. At the moment that the measured value equals or exceeds this programmed value, CM1 causes its output to transfer from Normal and to latch in the Not-Normal state, removing power from its NC terminal and supplying power to its NO terminal, leading to the following events:
 1. Removing power from NC terminal of CM1 removes power from C1. Its contacts return to the NO state and power is removed from M1 and CL1.
 2. When power is removed from terminal S of R1TD, a time delay function commences which causes power to continue to be supplied to coil R1 for approximately one (1) second, continuing the R1 latch.
 3. Providing power to the NO terminal of CM1 provides power to the coil of Solenoid Contactor 2 (C2), which becomes energized, closing the C2 NO contacts and energizing the Dropping Solenoid (SOL1) [#10].

When the approximately one (1) second time delay of R1TD is satisfied, the coil of R1 is de-energized and switches A and B return to Normal position, ending the R1 latch, removing power from the COM terminal of CM1.

The return of R1B to normal provides a path to ground for the reset terminal of CM1, unlatching it, returning CM1 to Normal. At this point, the circuit is ready for another cycle that can be begun by the closing of switch SW2.

The components illustrated in FIG. 7 and described in the above description of operation of electronic circuit 22 are readily available today by referring to the following chart which lists the components by their commercial identifications. The first column of numbers in the chart below correlates to the components/elements shown in the FIG. 7 schematic drawing and the second column indicates the number of each of such components/elements in circuit 22.

Skid Tester Control Circuit Components

| # | Qty | Component/element |
|---|-----|-------------------|
| 1 | 1 | Red Lion Motor Speed Control Module #IFMR0066 |
| 2 | 2 | White Rogers DC Power Contactor #120-106131 |
| 3 | 1 | Square D Momentary Pushbutton Switch #SKIL35GH13 |
| 4 | 1 | Square D Key Operated Switch #KS11K1 |
| 5 | 1 | Red Lion Rate Display #DT 700 000 |
| 6 | 1 | Buss Fuse holder #4406 |
| 7 | 1 | 2 amp fuse #3AG2 |
| 8 | 1 | Buss Fuse Holder #425060-1C |
| 9 | 1 | 30 amp fuse #LPJ-30SP |
| 10 | 1 | Syncrostat Solenoid #1502-12-C-2-U-1-B1 |
| 11 | 1 | Stearns Electric Clutch #CTS-35 |
| 12 | 1 | Leeson Motor #108046.00 |
| 13 | 1 | Red Lion Logic Magnetic Pickup #LMPC 0000 |
| 14 | 1 | Turck Releco Control Relay #C2-A20X |
| 15 | 1 | Turck Multicomat Off Delay Timer #CT2-A20/S |
| 16 | 1 | Turck Relay Base #C-8 |
| 17 |   | Wire |
| 18 |   | Connectors |

In operation of apparatus 20 on road surface 78 of a road 79, and incorporating the above description as part and parcel of the following description of the operation of apparatus 20, layers of glycerin (not shown) are first applied to flat 61 of tire 60 and to a patch of road surface 78 at which testing of flat 61 is to take place, to negate or remove factors involving humidity, extraneous contaminants of the road surface and which could affect an accurate and correct reading on tape 116. Thereafter, apparatus 20 is put into its O-position, FIGS. 1, 2, and 3, which is that:

a) apparatus 20 is set in a stationary mode by the connection of its hitch assembly 32 to a fixed, i.e., a non-moving support structure, such as a parked vehicle (not shown) to which assembly 32 is connected;

b) mechanism 80 is cocked by positioning end or latch 82 of bell-crank assembly 81 upon ledge 83 at the rear of apparatus 20;

c) adjusting sleeve 85 and its ledge 86 by which, say, a one-quarter (¼") inch span 98, is established between flat 61 and road surface 78;

d) door 108 is open, using an upward action on door lever 110 to provide projection of piston rod 104 past hole 106;

e) carriage 48 is positioned at the extreme rear of frame 24;

f) indicator 122 is seated against its reference point 123 on its bearing carrier 59 that is part of carriage 48, with constant-force coiled springs 40 coiled in their non-extended position on rear metal casting 39; and g) with console switch SW1 open.

The key switch SW1 of electrical control circuit 22 is closed, and the SW2 switch is closed. Motor 34 begins to accelerate, and electric clutch 65 engages to cause tire 60 to rotate with its axle 63, and tire 60 begins to rotate. Timing sensor 75 senses the movement of the sprocket wheel 71 and provides a digital signal that is proportional to the speed of motor 34. The digital signal is transmitted into the sensor input of the control module CM1 in circuit 22. CM1 analyses this signal and compares it to a programmed value say, for example, the programmed value being 50 miles per hour [mph] in control module CM1. At the moment the measured value of speed of the rotating tire 60 equals or exceeds the programmed value of 50 mph, the control module CM1 causes its output to transfer from Normal and to latch into a not-Normal state.

What now occurs in the non-Normal state is that:

a) motor 34 stops running and electrical clutch 65 is disengaged;

b) the solenoid 94 of dropping mechanism 80 is energized, the bell-crank mechanism 80 is actuated by reciprocating action of the solenoid's control or pull rod 93, and by which end or latch 82 is pulled off of its ledge 83;

c) apparatus 20 drops the tire 60 to the road surface 78 [Note: glycerin has been brushed onto the tire's tread]; and d) the momentum of tire 60 propels carriage 48 against the force of the constant-force coiled springs 40, to the right in FIG. 1. The momentum of the wheel 62 is damped by the force of these coiled springs, and carriage 48 ceases its movement to the right in FIG. 1. Wheel 62 and carriage 48 are retracted by the force of springs 40 until the piston rod 104 strikes the spring-biased closed door 108. In effect the piston rod 104 substantially cancels the collective force of springs 40.

However, in the carriage's movement to the right, the indicator's collar has slid along its tubing to its advanced position such as, for example, illustrated in FIG. 6, that is correlated to gauge tape 116 that is calibrated to the coefficient of friction of the road's surface to the rubber tire. The test is concluded by reading the particular gradation 120 of gauge tape 116 at the point of advancement or thrust of the indicator 122.

The driving and driven pulleys, FIGS. 2A, 2B, are selected to provide a wheel speed at a programmed value of CM1, equal to, for example, 50 mph. At this value, the testing apparatus includes a 22-toothed and a 30-toothed sprocket. The programmed value can be other than a 50 mph figure.

For the next testing operation, the unit is prepared to achieve its O position by these procedures:

1. The rear of carriage 48 is manually raised by knob 100 and the bell crank assembly 81 is re-set on ledge 83.

2. The door 108 is manually opened against the bias spring 112 so that piston rod 104 passes through hole 106.

3. The indicator 122 is slid back to where it is once again against its associated bearing carrier 59 of carriage 48.

Each of the components and elements of apparatus 20 is fabricated from known materials using standard and conventional techniques of manufacture. Assembly of apparatus 20 begins with assembly of the elements forming the frame and its sub-components, then the carriage, dropping mechanism, wheel assembly and electronic control systems, and can be readily achieved by knowledge of this disclosure.

Various modifications and changes can be made in apparatus 20 without departing from the spirit and scope of the appended claims to the invention.

INDUSTRIAL APPLICABILITY

The invention is useful in testing road surfaces such as, although not to be considered exhaustive, parking lot surfaces, sidewalks, airport runways, street intersections, manhole covers, bridge plates, decking, slurry coatings, asphalt, concrete, reprocessed road material, and roadway paint products.

I claim:

1. In an apparatus for testing the co-efficient-of-friction of a surface such as the surface of a road, the apparatus including
   a frame including longitudinally-extending members and being suitably mounted on a plurality of standards adapted to engage such surface,
   a plurality of standards supporting said frame,
   a carriage slidably mounted on said members,
   constant-force coiled spring means operatively connecting together said frame and carriage for retracting said carriage along said members upon completion of the testing operation by said apparatus,
   a tire securely mounted to a wheel rotatably mounted on said carriage,
   means on said frame for maintaining a span between the tire and such surface,
   means for rotating the wheel by which the tire rotates,
   a gauging tape in alignment with one of said members, and
   indicator means mounted on one of said members slidable with said carriage in a forward direction of motion for said carriage,
the improvement comprising
   said rotating means including a motor having a shaft on which a first sprocket wheel having teeth is securely mounted thereto and which accelerates the speed of said tire upon its actuation,
   electronic means for actuating said rotating means whereby said carriage slides in a direction of forward motion along said members,
   said electronic means including
      means for sensing the speed of said rotating means as the speed of said tire increases to reach the predetermined value in said electronic means, and
      means for releasing said maintaining means,
      whereby the tire drops to engage such surface and at which dropping said indicator means halts on said one of said members at a gauge reading to indicate the co-efficient of friction of the surface to which the tire drops.

2. The apparatus of claim 1 wherein
   a single one of said standards supports said frame at its rear, and
   said maintaining means comprises
      a bell-crank assembly having a pivotal mount pivotally mounted on and at the rear of said frame and having
      a first arm and a second arm on opposite sides of the pivotal mount,
      bearing means mounted on said first arm,
      means for pivoting the second arm on the other side of the pivotal mount,
      said single one of said standards including a latch means,
      said bearing means engaging said latch means in the cocked condition,
      whereby upon actuation of said pivoting means, said bell-crank assembly turns on its pivotal mount to disengage said bearing means from said latch means and thereby lower the frame on and one of said standards.

3. In the apparatus of claim 2 wherein
said pivoting means comprises
   solenoid means having a reciprocable rod and being fixedly connected to said frame which when energized retracts said rod thereby turning said second arm about the pivotal mount.

4. In the apparatus of claim 3 wherein
said solenoid means includes linkage connecting its rod to said second arm.

5. In the apparatus of claim 4 wherein
a single one of said plurality of standards is disposed at the rear of said frame and comprises
   a threaded stem,
   said latch means is threadedly mounted on said stem, and
   handle means securely mounted to said latch means for adjusting said latch means along the length of said stem,
   whereby the position of the cocked condition of said mechanism to said frame is adjustable along the length of said stem.

6. In the apparatus of claim 5 wherein
said latch means comprises
   a threaded sleeve and a ledge at its bottom on which said bearing means seats in a cocked condition for said mechanism.

7. In the apparatus of claim 6 wherein
said bearing mean comprises
   a roller.

8. In the apparatus of claim 1 wherein
the wheel includes an axle,
said rotating means further comprising
   a second sprocket wheel secured to said axle, and
   a toothed pulley drive belt operatively connecting the first sprocket wheel and second sprocket wheel together.

* * * * *

UNITED STATES PATENT AND TRADEMARK OFFICE
CERTIFICATE OF CORRECTION

| | | |
|---|---|---|
| PATENT NO. | : 6,681,614 B1 | |
| DATED | : January 27, 2004 | |
| INVENTOR(S) | : Daniel L. Riffe | |

It is certified that error appears in the above-identified patent and that said Letters Patent is hereby corrected as shown below:

Column 9,
Line 6, delete claim 1 as it reads, and substitute the claim 1 below:
-- 1.
In an apparatus for testing the co-efficient-of-friction of a surface such as
  the surface of a road, the apparatus including
a frame,
a plurality of standards adapted to engage the surface supporting
  said frame, said frame including fixedly-mounted longitudi-
  nally-extending members thereon,
a carriage slidably mounted on said longitudinally-extending members,
constant-force coiled spring means operatively connecting together
  said frame and carriage for retracting said carriage along said
  members upon completion of the testing operation by said
  apparatus,
a tire securely mounted to a wheel rotatably mounted on said carriage,
means on said frame for maintaining a span between the tire and the
  surface,
means for rotating the wheel by which the tire rotates,
a gauging tape in alignment with one of said fixedly-mounted
  members, and
indicator means mounted on one of said members slidable with said
  carriage in a forward direction of motion for said carriage,
the improvement comprising
said rotating means including a motor having a shaft on which a first
  sprocket wheel having teeth is securely mounted thereto, said
  motor accelerating in its operation the speed of said tire,
electronic means for actuating said rotating means whereby said
  carriage slides in a direction of forward motion along said
  fixedly-mounted members,
said electronic means including
means for sensing the speed of said rotating means as the speed of said
  tire increases to reach a programmed value in said electronic
  means,
said sensing means comprising
a timing sensor employed immediately next to said sprocket wheel for
  counting the number of teeth of said sprocket wheel that passes it
  in a given period of time, the motion of the number of teeth
  passing said sensing means generating a signal that is transmitted
  by said timing sensor to and processed by said electronic means
  for comparing the rotational speed corresponding to the signal to

UNITED STATES PATENT AND TRADEMARK OFFICE
CERTIFICATE OF CORRECTION

PATENT NO. : 6,681,614 B1
DATED : January 27, 2004
INVENTOR(S) : Daniel L. Riffe It is certified that error appears in the above-identified patent and that said Letters Patent is hereby corrected as shown below:

Column 9 (cont'd),
      the programmed value in said electronic means to obtain results
      indicating the accurate co-efficient-of-friction of the surface, and
means in said electronic means for releasing said maintaining means
      upon the programmed value in said electronic means being
      reached,
whereby the tire upon dropping to the surface by release of said
      maintaining means when the programmed value is reached in the
      electronic means the accurate co-efficient-of-friction of the
      surface is measured by the halt of said indicator means on its
      fixedly-mounted member. --.

Column 10,
Line 13, change "and" (second occurrence) to -- said --.

Signed and Sealed this

Thirteenth Day of July, 2004

JON W. DUDAS
*Acting Director of the United States Patent and Trademark Office*